United States Patent [19]

Choi et al.

[11] Patent Number: 5,157,157
[45] Date of Patent: Oct. 20, 1992

[54] PROCESS FOR PREPARING 1-OXO-1,2,3,4,-TETRAHYDRONAPHTHA-LENE

[76] Inventors: Myoung J. Choi, 391, Doryong-Dong; Kyu W. Lee, 384-24, Doryong-Dong, both of Yuseong-Gu, Daejeon-Jikhalsi, Rep. of Korea

[21] Appl. No.: 710,837

[22] Filed: Jun. 4, 1991

[30] Foreign Application Priority Data

Jun. 7, 1990 [KR] Rep. of Korea ............... 90-8343

[51] Int. Cl.$^5$ .............................. C07C 45/36
[52] U.S. Cl. ............................................ 568/321
[58] Field of Search ................................ 568/321

[56] References Cited

U.S. PATENT DOCUMENTS 4,175,098 11/1979 Mizukami et al. .......... 568/321
4,753,911 6/1988 Goe et al. ........................ 568/321

FOREIGN PATENT DOCUMENTS 50-58044 5/1975 Japan .............................. 568/321
197708 8/1977 U.S.S.R. .......................... 568/321

Primary Examiner—James H. Reamer
Attorney, Agent, or Firm—Kenyon & Kenyon

[57] ABSTRACT

This invention relates to a process for preparing 1-oxo-1,2,3,4-tetrahydronaphtahalene(α-tetralone) in high yield and high selectivity from the liquid phase oxidation of tetralin in a bubble column reactor under several homogeneous and heterogeneous catalyst systems such as hexavalent chromium oxide, silica-supported chromium oxide, and insoluble material from the homogeneous oxidation mixture in N,N-dialkyl acid amides.

5 Claims, 1 Drawing Sheet

PROCESS FOR PREPARING 1-OXO-1,2,3,4,-TETRAHYDRONAPHTHALENE

FIELD OF THE INVENTION

This invention relates to a process for preparing 1-oxo-1,2,3,4-tetrahydronaphthalene in the presence of a catalyst comprising organochromium component. More specifically the invention comprises a process for preparing 1-oxo-1,2,3,4,-tetrahydronaphthalene (formula I), a precursor of α-naphthol, in high selectivity and high yield, through an oxidation of tetralin using an organochromium catalyst in solution.

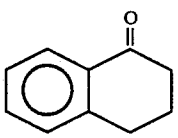

(I)

BACKGROUND OF THE INVENTION 1-oxo-1,2,3,4-tetrahydronaphthalene (also known as "α-tetralone") is generally known as a precursor of α-naphthol(A), which has been widely used as an intermediate of agricultural chemicals, pharmaceutical, dyes, and various precision-required chemicals.

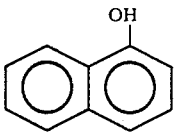

(A)

It is well known that the catalytic liquid phase oxidation of tetralin (formula II), which has four comparatively weak C—H bonds, produces α-tetralyl hydroperoxide, α-tetralone, and α-tetralol. All of the above are oxidized only at the α - position, using molecular oxygen as an oxidant and a metal ion catalyst in the presence or absence of solvents.

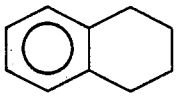

(II)

α-tetralyl hydroperoxide is obtained in high selectivity from the oxidation of tetralin (Japanese Patent Laid Open No. 54-10248).

Subsequently, α-tetralone was prepared by decomposing α-tetralyl hydroperoxide under metal ion catalysts.

α-tetralone may also be prepared by the direct liquid phase oxidation of tetralin under catalysts such as the chromium salt, cobalt salt, pyridines, or amines (U.S. Pat. No. 3,404,183, Japanese Patent Laid Open No. 49-135958, 50-112347 and 51-48643).

However, a method for obtaining α-tetralone by the decomposition of peroxides has some recognized disadvantages. The reaction results in lower conversion and a slower reaction rate due to the handling requirements that thermally sensitive compounds demand and the need for low peroxide concentrations.

Furthermore, the direct oxidation method using cobalt salt and so on to obtain α-tetralone, also has some disadvantages. The decomposition rate for the produced peroxides was increased by a cobalt catalyst which caused the concentration of α-tetralone, a by-product in this reaction to increase, as a result, the selectivity for the desired ketone decreased.

In addition, a great deal of investment in operation and design of facilities in separating α-tetralone from α-tetralol become necessary because the temperature difference between α-tetralol and α-tetralone is only 2–3° C. at the same vapor pressure.

Accordingly, an α-tetralone fraction, containing 5–60% of α-tetralol, is usually used as the raw material in the dehydrogenation reaction. In this case, the rate for dehydrogenation of α-tetralol is very rapid and readily converted to naphthalene through further dehydrogenation of the 1,2-dihydronaphthalene intermediate. However, naphthalene, a compound that has sublimation property and is used as an insecticide because of its toxicity, reduces the activity of the catalyst in the catalytic dehydrogenation reaction by being adsorbed at the surfaces and pores of the catalyst.

Especially, the use of the chromium salt instead of the cobalt salt markedly increases the ratio of α-tetralone to α- tetralol. However, the economic aspects of the process, such as safety, high cost of pyridine, slow reaction rate, and efficiency of recovery, renders the process unfavorable since a large amount of pyridine solvent is used.

In addition, liquid phase oxidation under a pyridinium salt catalyst, in the absence of solvent, exhibits high concentrations of α-tetralyl hydroperoxide. However, this process is also unfavorable since the same problems such as control and safety of the reaction, are seen.

A process for preparing α-tetralone by oxidation of tetralin, in high selectivity, under a catalyst system in which the soluble chromium or cobalt salt is dissolved in N,N-dialkyl acid amides such as dimethylformamide(DMF), dimethylacetamide(DMA), and diethylacetamide(DEA), is reported in Japanese Patent Laid Open No. 541-14950. In this process, a homogeneous solution is obtained by dissolving the metal salts in the solvent mentioned above. The peroxide is diluted sufficiently to a safe concentration range, and the product yield can be increased by promoting the decomposition reaction of peroxides.

In the above case, the catalytic soluble metal salts such as acetate, propionate, stearinate, and naphthenate salts are used as the soluble cobalt or chromium salt showing about 30% of conversion. The catalytic activity of these salts is thought to be a result of the formation of a chromium or cobalt complex with the N,N-dialkyl acid amide as a bidentate ligand. But, according to the above processes, the product yield was decreased because of a higher concentration of by-product.

The technology for using the 8th group noble metal complex catalyst with the biphyllic ligand is reported in U.S. Pat. No. 3,422,147. The use of the chromium oxide complex catalyst using lutidine as a ligand, complex catalyst between the chromium salt of organic acids and the pyridine derivatives are reported in Japanese Patent Laid Open No. 50-58044 and 50-112347 respectively. The use of chromium acetylacetonate is disclosed in Japanese Patent Laid Open No. 60-19744. However, all of the above processes suffer from low yields ranging from about 25.1 to about 33.4%.

An object of the present invention is to provide an improved and economic process for preparing α-tetralone through the liquid phase oxidation of tetralin in high selectivity and high yield.

Figure 1:
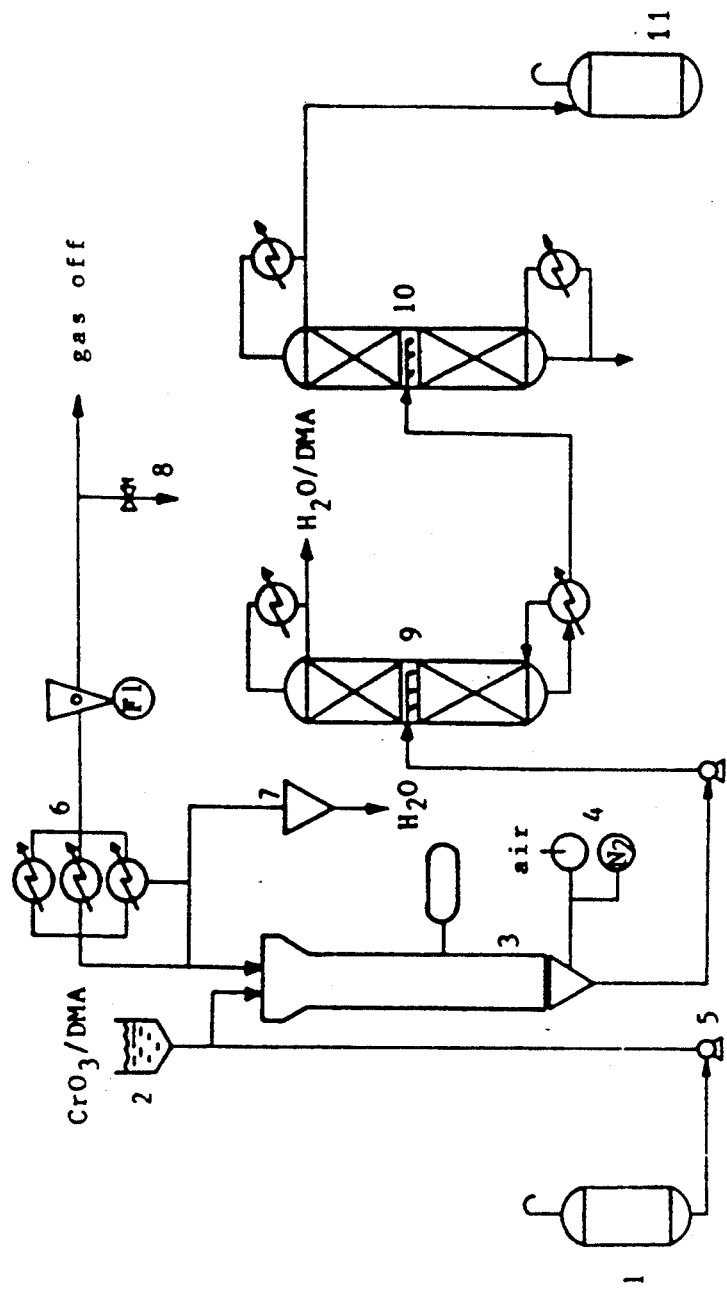
FIG. 1 shows a schematic diagram embodying the process of manufacturing aromatic ketone in the presence of catalyst according to the invention.

| 1 - tetralin storage tank | 2 - catalyst solution |
| 3 - bubble column reactor | 4 - nitrogen tank |
| 5 - pump | 6 - condenser |
| 7 - water separator | 8 - oxygen meter |
| 9 - distillation unit for low boiling point material | |
| 10 - solvent distillation unit | 11 - tetralone storage tank |

DESCRIPTION OF THE INVENTION

The present invention is a process for preparing 1-oxo-1,2,3,4-tetrahydronaphthalene ($\alpha$-tetralone) from tetralin under a metal catalyst, characterized by the fact that tetralin is oxidized in a bubble column reactor using a homogeneous catalyst solution formed from dissolving hexavalent chromium oxide in N,N-dialkyl acid amide.

Examples of N,N-dialkyl acid amides include N,N-dimethylformamide, N,N-dimethylacetamide, and N,N-diethylformamide, and 40-60 times in volume being equivalent to the hexavalent chromium oxide can be preferably used in this invention.

Further, in accordance with the invention, $\alpha$-tetralone can be prepared by the oxidation of tetralin in a bubble column reactor under a heterogeneous metal catalyst system prepared by dispersing a silica-supported solid catalyst in the N,N-dialkyl acid amide. In this case, the solid catalyst should have a particle size of about 45-150 $\mu$m and about 0.01-1 wt % chrome content.

In addition, $\alpha$-tetralone can be prepared by the oxidation of tetralin in a bubble column reactor using less than 40 $\mu$m of insoluble material recovered from the above mentioned homogeneous catalytic oxidation mixture.

In this invention, two types of catalyst systems, i.e., homogeneous catalyst dissolving hexavalent chromium oxide directly in N,N-dialkyl acid amide ligand or heterogeneous catalyst dispersing silica-supported chromium oxide in N,N-dialkyl acid amide, exhibited better reactivity than the reported methods in the liquid phase oxidation of tetralin through a bubble column reactor as depicted in FIG. 1.

According to this invention, when the hexavalent chromium oxide was directly dissolved in dimethylacetamide, a considerable amount of heat and flame was generated because of the oxygen gas formed from the highly oxidic hexavalent chromium oxide. This being so, various experiments to get the standard mixing ratio were performed on the aspect of safety working. As a result, after the hexavalent chromium oxide was exposed to air, it did not generate any heat and flame on dissolving in dimethylformamide, and exhibited reduced oxidizing power because of its highly hygroscopic property.

Accordingly, chromium oxide should be dissolved in a solvent directly after being powderized. The volume ratio of solvent to the hexavalent chromium oxide can be 30-100 times, preferably 40-60 times and more preferably and safely 45-47 times.

Namely, the ratio of $\alpha$-tetralone to $\alpha$-tetralol in this process can be within 40 to 60 it has less formation of by-product, 40-50% of conversion, 38.4-46.5% of yield, 93-96% of selectivity to $\alpha$-tetralone, which are markedly enhanced results when compared to the previously reported 27-38% of conversion, 25.1-33.4% of yield, and 88-93% of selectivity.

These reactivity results were obtained quantitatively through repeated gas chromatographic analysis with a capillary column using an internal standard method. Each component was actually separated through column chromatography using a mixed solvent system of n-hexane and ethyl acetate as an eluent. The components were finally identified by measuring the weight of each component separated from the vacuum distillation apparatus designed to control the reflux ratio of each component.

The homogeneous catalyst system of this invention is prepared by dissolving hexavalent chromium oxide in dimethylacetamide which is used as both ligand and solvent, and represents high selectivity and 13-23% of more enhanced conversion than other reported catalyst systems.

In the oxidation reaction with the soluble catalyst, very small amounts of fine particle material was precipitated out from the dispersed solution as the reaction proceeded. The precipitate was separated out after settling for a substantial period, and the physical properties were determined. As shown in Table 1, it was a very fine powder with average particle size being less than 50$\mu$m. The powder exhibited very low solubility in acid or alkali and was entirely insoluble in organic solvents or aqueous solution.

TABLE 1

Test on solubility and physical properties of insoluble material and chromium Oxides (III, VI) in various solvents.

| Classification | $H_2SO_4$ | HCl | $HNO_3$ | NaOH | $H_2O$ | $CH_3OH$ | DMA | Acetone |
| --- | --- | --- | --- | --- | --- | --- | --- | --- |
| Insoluble Material | is | ss | ss | is | is | is | is | is |
| $Cr_2O_3$ | is | is | is | is | is | is | is | is |
| $CrO_3$ | is | ss | is | s | s | s | is | s |

Notes:
average particle size of insoluble material-49.5 $\mu$m (measured with Coulter-counter Model TA-~)
ss : slightly soluble
s : soluble
'is' : insoluble The molar ratio between $\alpha$-tetralone and $\alpha$-tetralol forming a side product under the catalyst used, was within 40-60. This ratio is significantly better than the previously reported 13-30 molar ratio obtained with chromium acetate complex catalyst.

Accordingly, about 0.3wt% of insoluble material contained in the reaction mixture can be used as a homogeneous catalyst in preparing $\alpha$-tetralone by the oxidation reaction. The insoluble material can be recovered in more than 95% from the oxidation reaction mixture, and can be used more than 4 times without losing any catalytic activity through repeated recovery.

From this result, the catalytic liquid phase oxidation of tetralin using a heterogeneous catalyst was studied with an improved Phillips catalyst among the commercial catalysts. And for the purpose of testing activities of some heterogeneous catalysts, various supported chromium oxide, which exhibit catalytic activity in the liquid phase slurry polymerization of ethylene, were dispersed in N,N-dialkyl acid amides and it also exhibited catalytic activity.

In this case, the alkyl substituents on the N-atom were methyl groups in all cases and hydrogen, methyl and ethyl groups were possible as carbonyl substituents. Dimethylacetamide especially exhibited markedly enhanced activity compared with dimethylformamide.

The solid particle which acts as supporting material for the heterogeneous catalyst, improved from the reported Phillips catalyst having a particle size of 45–150 $\mu$m and a chrome content lower than 1% by weight, is characterized by the smaller particle size and lower chrome content than the Phillips catalyst.

The catalyst according to this invention did not exhibit any activity in itself, but exhibited high activity when it was used with suitable amount of N,N-dialkyl acid amide as a ligand. N,N-dialkyl acid amides having the general formula of $R_3 CONR_1R_2$ were used as ligands wherein $R_1$ and $R_2$ are methyl, and $R_3$ is hydrogen, methyl or ethyl.

From this result, it can be considered that dimethylacetamide, which has higher electron donating power when compared with dimethylformamide causes the enhancement of the activity of the complex formed from the peroxy radical, chromium ion, and dimethylacetamide in the reaction system, eventually producing $\alpha$-tetralone directly not through the radical of $\alpha$-tetralone.

Moreover, in the case of using N,N-dialkyl acid amides (e.g. dimethylformamide and dimethylacetamide) as solvents, the reaction selectivity is known to be more markedly enhanced than in the case of using acetic acid as a solvent because of the reduced reaction rate.

A strong coordinate bond of N,N-dialkyl acid amide with chromium ion compared with $H_2O$, $RCOO^-$, and RCOOH ligands(herein, R is hydrogen, methyl or ethyl), makes the exchange reaction between the peroxide formed and N,N-dialkyl acid amide difficult, and then the selectivity to $\alpha$-tetralone is enhanced.

In addition, the reactivity tends to increase according to the electron donating ability of the alkyl group, but the price of diethylacetamide is about 3 times more expensive than that of dimethylacetamide, so dimethylacetamide is desirably as the solvent and ligand in this invention.

And, the hexavalent chromium oxide or improved Phillips catalyst in some solvents which are different in physical properties such as surface area and pore size, can be used to get higher catalytic activity in the gas-liquid or gas-liquid-solid 3-phase heterogeneous reaction, respectively.

The physicochemical properties of the catalysts used in this invention with each of the different supporting materials are summarized in Table 2.

TABLE 2

The physicochemical properties of various chrome/silica supporting materials of heterogeneous catalysts

| properties | | supporting materials | | | |
|---|---|---|---|---|---|
| | | A | B | C | D |
| surface area (m$^2$/g) | | 373 | 333 | 309 | 321 |
| pore size (ml/g) | | 2.56 | 2.03 | 1.95 | 1.10 |
| average diameter of pore (Å) | | 137 | 122 | 126 | — |
| particle size range ($\mu$m) | | 45–150 | | | |
| weight loss % (at 110° C.) | | 2.5 | 1.9 | 1.9 | — |
| total volatility (wt %) (960° C.) | | 7.9 | 10.8 | 12.4 | 9.5 max |
| Composition | wt % SiO$_2$ | Balance | Balance | Balance | 97.0 min. |
| | wt % Cr | 0.98 | 1.07 | 0.95 | 0.97–1.28 |
| | wt % SO$_4$ | — | — | — | 0.5 max |
| | wt % Al$_2$O$_3$ | — | — | 3.94 | 0.20 |
| | wt % Ti | — | 1.08 | — | — |
| | ppm Na$_2$O | 150 | 150 | 150 | 0.25 max |
| | ppm Fe$_2$O$_3$ | <50 | <50 | <50 | — |

Notes
each number denotes the analytical value before activation
A, B, C : products (A ; C-34300MS, B : C-23302, C ; C-23340) of PQ Corp.
D : product (969 ID) of Phillips Petroleum Co.

In this invention, the temperature of the oxidation reaction was maintained at 70–110° C., and the flow rate of air was adjusted to the amount of gas in the reactor to be equal during the oxidation reaction. The length of the bubble column reactor Was 313.5 mm, which is 11 times longer than the diameter. The defoamer was attached to prevent the foam development owing to the linear velocity of the introducing air.

Specifically, air as an oxidizing gas in this invention was introduced through a gas distributer made of 50 mesh sintered glass for the mass transfer effect of oxygen bubble to be improved.

As a result, the reaction efficiency was maximum at 90 ± 1° C. of reaction temperature, and the amount of gas in the reactor was maintained equally when the gas flow rate was 700 ± 10cc/min.

Especially, the condenser was connected in a three-step parallel manner such that the reactant and product did not escape to the upper part of the bubble column reactor. With this apparatus and under the temperature and gas flow rate already mentioned, the oxidation reactivity of tetralin with the catalyst in this invention was measured as a function of reaction time, and exhibited a tendency to increase after a certain some induction period, then decreased, although there were some differences in the slope of oxygen absorption rate profile as the catalysts were changed.

From this result, the reaction rate could be predicted because it corresponded well with the concentration profile of the peroxides, conversion, and selectivity of $\alpha$-tetralone in the oxidation reaction mixture.

A more detailed description of this invention according to the attached schematic diagram FIG. 1, is as follows :

In FIG. 1, tetralin is introduced from the storage tank(1) to the upper part of the reactor by the pump(5), and the ready-prepared catalyst solution(2) is introduced simultaneously. Nitrogen gas is injected in to the bubble column reactor(3) to which air and the nitrogen tank are connected.

After maintaining the temperature as mentioned above, the reaction is carried out for 390 min in the bubble column reactor of gas-liquid or gas-liquid-solid phase maintaining an equal amount of gas in the reactor throughout the reaction.

At this time, the water produced from the reaction is condensed and collected in the Dean-Stark type water separator(7), and each component in the reaction mixture which are evaporated by the injected gas stream are condensed by the 3-step parallel condenser(6), and then circulated.

From the gases which have passed through the condenser(6) is measured the oxygen concentration absorbed in the reaction by the oxygen meter(8), and is exhausted to the outside. After the oxidation reaction is finished, the reaction mixture is transferred to the fractional distillation unit(9) for low boiling point material and solvent distillation unit(10) for ketone and alcohol, and recovery of unreacted material and separation and purification of the product are performed there.

As described in more detail, α-tetralone, a precursor of a α-naphthol, can be prepared in high selectivity and high yield by using the hexavalent chromium oxide dissolved in certain solvents according to this invention.

The following examples are intended to illustrate but not to limit the scope of the present invention.

Example 1 illustrates the gas-liquid phase oxidation reaction by homogeneous catalyst, and examples 2-8 illustrate 3-phase(gas-liquid-solid) slurry reaction under each catalyst condition.

EXAMPLE 1

The catalyst solution was prepared by dissolving 0.116g of powderized hexavalent chromium oxide in 29.2ml of dimethylacetamide immediately. A bubble column reactor (28.5mm × 313.5mm of diameter × height) having a gas distributer, made of 50 mesh sintered glass attached and defoamer connected to the upper part was used. 146.4ml of tetralin was added to the bubble column under a nitrogen gas stream. Ready-prepared catalyst solution was added thereto.

The temperature of the reaction mixture was controlled to 90 ± 1° C. by operating a temperature controller. Nitrogen gas was changed to air and introduced continuously at a rate of 700 ±10 cc/min.

After about 10 min, water formed from the dissociation of peroxides and was collected in the Dean-Stark water separator. The reaction mixture which was evaporated with the air was condensed by the 3-step parallel condenser attached to the upper part of the reactor, and it was circulated.

The oxygen concentration of the exhaust gas was measured with an oxygen meter(Servomex 570A) after being passed through a dry-ice trap.

After sampling the reaction mixture at certain intervals, the peroxide value was measured by iodometric titration, and analyzed with 30mm × 0.32mm of SPG-2 capillary column.

After about 390 min, the oxidation reaction mixture, a less viscous brownish liquid, was cooled immediately and was recovered from the reactor by a teflon piston pump.

The concentration of peroxides was measured by iodometric titration and the concentration of each component was analyzed by G.C. The calculated conversion and selectivity to α-tetralone were calculated to be 39.2% and 96.1%, respectively.(Yield 37.7%).

EXAMPLE 2

Using the same apparatus and following the procedure as in example 1, chrome/silica catalyst(D) having 321 $m^2/g$ of surface area, 1.10 ml/g of pore volume, and 45-150 μm of particle size was used as supporting material. The catalyst solution was prepared by dispersing this catalyst in 29.2 ml of DMA.

To the bubble column reactor Was added 146.4 ml of tetralin under a nitrogen gas stream. The reaction was performed following the same procedure as described in example 1, affording the pale yellow oxidation reaction mixture. The catalyst was recovered by filtration.

The conversion and selectivity to α-tetralone, which was measured and calculated from the peroxide value and capillary G.C. of the reaction mixture, were 49.5% and 96.8% respectively. (Yield 47.9%).

EXAMPLE 3

Using the same apparatus and following the procedure as in example 1, the catalyst solution was prepared by dispersing chrome/silica catalyst(B) having 333 $m^2/g$ of surface area, 2.03 ml/g of pore volume, and 45-150 μm of particle size in 29.2 ml of DMA. A pale-yellowish oxidation reaction mixture was obtained by performing the reaction under the same concentration of reactant and reaction conditions as described in examples 1 and 2.

The measured and calculated conversion and selectivity to α-tetralone were 40.9% and 96.2% respectively. (Yield 39.3%)

EXAMPLE 4

Using the same apparatus and following the procedure of example 1, the catalyst solution was prepared by dispersing chrome/silica catalyst(C) having 309 $m^2/g$ of surface area, 1.95 ml/g of pore volume, and 45-150 μm of particle size in 29.2 ml of DMA. A pale-yellowish oxidation reaction mixture was obtained by performing the reaction under the same procedure as described in example 2.

The measured and calculated conversion and selectivity to α-tetralone were 39.6% and 95.3% respectively. (Yield 37.7%)

EXAMPLE 5

Using the same apparatus and following the procedure as in example 1, the catalyst solution was prepared by dispersing chrome/silica catalyst(A) having 373 $m^2/g$ of surface area, 2.56 ml/g of pore volume, and 45-150 μm of particle size in 29.2ml of DMA. The reaction was performed under this catalyst solution following the same procedure as described in example 2. The product was obtained as a pale-yellowish liquid.

After analyzing the oxidation reaction mixture, the measured and calculated conversion & selectivity to α-tetralone were 39.6% and 95.2% respectively. (Yield 37.7%)

EXAMPLE 6

Using the same apparatus and following the procedure as in example 1, the catalyst solution was prepared by dissolving 0.116 g of powderized hexavalent chromium oxide in 29.2 ml of dimethylformamide immediately. The pale-brownish oxidation mixture was obtained by performing the reaction under the same procedure as described in example 1.

From the analysis of the reaction mixture, the measured and calculated conversion & selectivity to α-tetralone were 32.8% and 30.5% respectively. (Yield 26.4%)

EXAMPLE 7

Using the same apparatus and following the procedure as in example 1 the catalyst solution was prepared according to the same ratio as in the homogeneous catalyst. The catalytic activity of a dark-brownish insoluble material was tested having 39.5 μm of average particle size which was settled down and recovered from the oxidation reaction mixture of example 1.

Namely, catalytic solution was prepared by dispersing 0.116 g of above mentioned insoluble material in 29.2 cc of dimethylacetamide. The oxidation reaction was performed according to the same procedure as described. A dark-brownish reaction mixture was obtained.

From the analysis of reaction mixture, the calculated conversion and selectivity to α-tetralone were 23.2% and 95.9% respectively. (Yield 22.2%)

EXAMPLE 8

The oxidation reaction was performed according to the procedure described in example 7 using 0.232 g of insoluble material recovered in example 1.

From the analysis of the dark-brownish reaction mixture, the calculated conversion and selectivity to α-tetralone was 25.3% and 97.1% respectively. (Yield 24.6%)

What is claimed is:

1. A process for preparing 1-oxo-1,2,3,4,-tetrahydronaphthalene by oxidizing tetralin using a metal catalyst containing a chromium compound in N,N-dialkyl acid amide, comprising preparing a heterogeneous catalyst by dispersing silica-supported solid hexavalent chromium oxide catalyst in N,N-dialkyl acid amide, then oxidizing tetralin in a bubble column reactor in the presence of said heterogeneous catalyst.

2. The process as defined in claim 1, wherein the said solid catalyst has 45-150 μm of particle size.

3. The process as defined in claim 1, wherein the chrome content of said solid catalyst is 0.01-1 wt%.

4. The process as defined in claim 2, wherein the chrome content of said solid catalyst is 0.01-1 wt%.

5. The process as defined in claim 1, wherein the volume ratio of hexavalent chromium oxide catalyst in N,N-alkyl acid amide is 40 to 60 times.

* * * * *